US008071558B2

(12) United States Patent
Tokuda et al.

(10) Patent No.: US 8,071,558 B2
(45) Date of Patent: Dec. 6, 2011

(54) APPLICATION OF D-PSICOSE TO SUPPRESSION OF ABNORMAL CIRCADIAN INCREASE IN BLOOD GLUCOSE LEVEL

(75) Inventors: Masaaki Tokuda, Kagawa (JP); Ken Izumori, Kagawa (JP); Tatsuhiro Matsuo, Kagawa (JP); Kenji Morimoto, Kagawa (JP); Kaoru Takekawa, Kagawa (JP)

(73) Assignee: Rare Sugar Production Technical Research Laboratories, LLC., Kita-gun (JP)

( * ) Notice: Subject to any disclaimer, the term of this patent is extended or adjusted under 35 U.S.C. 154(b) by 636 days.

(21) Appl. No.: 11/909,493

(22) PCT Filed: Mar. 22, 2006

(86) PCT No.: PCT/JP2006/305692
§ 371 (c)(1),
(2), (4) Date: Sep. 11, 2008

(87) PCT Pub. No.: WO2006/101118
PCT Pub. Date: Sep. 28, 2006

(65) Prior Publication Data
US 2009/0062215 A1    Mar. 5, 2009

(30) Foreign Application Priority Data

Mar. 23, 2005  (JP) ................................ 2005-082948

(51) Int. Cl.
*A61K 31/7004*    (2006.01)
*A61P 3/08*    (2006.01)
(52) U.S. Cl. ....................................................... 514/25
(58) Field of Classification Search ........................ None
See application file for complete search history.

(56) References Cited

U.S. PATENT DOCUMENTS
2005/0245459 A1    11/2005    Izumori et al.

FOREIGN PATENT DOCUMENTS

| JP | 2001-11090 A | 1/2001 |
| JP | 2005-213227 A | 8/2005 |
| WO | 03/097820 A1 | 11/2003 |

OTHER PUBLICATIONS

Matsuo T. et al., J Nutr Sci Vitaminol "D-psicose is a rare sugar that provides no energy to growing rats", vol. 48, issue 1, pp. 77-80 (only abstract provided), published Feb. 2002.*
Merriam Webster Online Dictionary "Sugar"; also available at http://www.merriam-webster.com/dictionary/sugar; last viewed Oct. 27, 2010.*
Merriam Webster Online Dictionary "derivative"; also available at http://www.merriam-webster.com/dictionary/derivative; last viewed Jul. 15, 2009.*
International Search Report of PCT/JP2006/305692, date of mailing May 30, 2006.

* cited by examiner

*Primary Examiner* — Shaojia Anna Jiang
*Assistant Examiner* — Bahar Schmidtmann
(74) *Attorney, Agent, or Firm* — Westerman, Hattori, Daniels & Adrian, LLP

(57) ABSTRACT

A novel use of D-psicose (for suppressing the abnormal intra-day increase of blood glucose level) is provided. A composition containing D-psicose as the active component and for use in suppressing the abnormal intra-day increase of plasma glucose concentration. The composition is a composition in blend with D-psicose and/or a derivative thereof. The composition is in a form selected from sweeteners, seasonings, food additives, food materials, food and drink products, health food and drink products, pharmaceutical products, and feeds and blended with D-psicose, and/or a derivative thereof as the active component, for use in preventing and therapeutically treating diseases requiring the saving of insufficient insulin, the amelioration of insulin sensitivity and the amelioration of hyperglycemia, and/or diseases of which the symptoms can be ameliorated via the suppression of the abnormal intra-day increase of plasma glucose concentration or of which the onset can be prevented via the suppression thereof, such as diabetes mellitus, occult diabetic states, obesity, hyperglycemia, and/or arteriosclerosis. A method for using D-psicose in suppressing the abnormal intra-day increase of plasma glucose concentration, comprising giving D-psicose at given times to suppress the abnormal increase of plasma glucose concentration throughout the day.

8 Claims, 9 Drawing Sheets

APPLICATION OF D-PSICOSE TO SUPPRESSION OF ABNORMAL CIRCADIAN INCREASE IN BLOOD GLUCOSE LEVEL

TECHNICAL FIELD

The present invention relates to a technique for using D-psicose in suppressing the abnormal intra-day increase of plasma glucose concentration (blood glucose level). More specifically, the invention relates to the application of the action of D-psicose to suppress the abnormal intra-day increase of plasma glucose concentration (blood glucose level) by incorporating or orally administering D-psicose in foods or drinks in forms of sweeteners, seasonings, food additives, food materials, foods and drinks, health food and drink products, pharmaceutical products and feeds, where the action of D-psicose is based on D-psicose actions such as the elevation of the uptake of blood glucose in liver and muscle, the inhibition of sugar digestive enzymes in the gastrointestinal tract, the inhibition of sugar absorption from the gastrointestinal tract and the stimulation of insulin secretion from pancreas.

BACKGROUND ART

D-Psicose is one of monosaccharides called rare sugar. Because the sugar was hardly available in the past since the sugar could not be produced at a mass scale, almost no research works about the physiological activity and pharmacological activity of the sugar were done. In recent years, a mass-scale process of producing D-psicose with an enzyme has been developed by Izumori, et al. at the Agricultural Department, Kagawa University, so that the biological activity thereof has been elucidated.

Compared with monosaccharides such as D-glucose and D-fructose, D-psicose has been drawing attention as a sugar never promoting fat synthesis or never accumulating body fats, particularly intraperitoneal fat (non-patent reference 1). Additionally, a report tells that the effective energy value of D-psicose is almost zero (non-patent reference 2). Highly possibly, a process of producing D-psicose in a form of a crystalline sugar complex containing D-fructose will be established (patent reference 1). Therefore, an application of D-psicose as a sweetener is expected.

Concerning the physiological activity and pharmacological activity of D-psicose, the patent reference 1 includes a report telling that examinations were made using D-psicose and the intestinal tract about the influence of the ketohexose belonging to rare sugar on glucose absorption since foods are digested to decomposed so that glucose is absorbed in the intestine for supply; an action of D-psicose to mildly suppress blood glucose level was verified in an animal (rat), so that it was verified that D-psicose had an action of decreasing blood glucose at hyperglycemia and an action of promoting insulin secretion and that D-psicose hardly triggered protein saccharification. The patent reference 1 describes that it was demonstrate that the ketohexose belonging to rare sugar had an action of stimulating insulin secretion from pancreatic β cell and an action of enhancing insulin secretion at hyperglycemic states and that the ketohexose belonging to rare sugar will therefore expectantly be a substance with a new action mechanism never found conventionally; additionally that the ketohexose belonging to rare sugar promotes insulin secretion in patients with diabetes mellitus to ameliorate the blood glucose level; that the ketohexose belonging to rare sugar after enteral administration suppresses glucose absorption and the ketohexose belonging to rare sugar never influences sugar metabolism, which suggests that the ketohexose possibly suppresses post-meal hyperglycemia in diabetes mellitus so the ketohexose is expectantly a substance advantageous for the prevention or therapeutic treatment of diabetes mellitus; that it is observed that the ketohexose belonging to rare sugar is effective for preventing arteriosclerosis in significant relations with diabetes mellitus and complications thereof and the main cause of death due to diabetes mellitus is an arteriosclerotic disease, so the ketohexose belong to rare sugar and having an action of suppressing arteriosclerosis is expectantly an innovative therapeutic agent of diabetes mellitus to ameliorate the blood glucose level and prevent arteriosclerosis; and that the ketohexose belonging to rare sugar is expectantly a health supplementary food with such therapeutic effects and an anti-obesity action.

Non-patent reference 1: Matsuo T., et al., Asia Pacific J. Clin. Nutr. 10, 233-237, 2001

Non-patent reference 2: Matsuo T., et al., J. Nutr. Sci. Vitaminol 48, 77-80, 2002

Patent reference 1: International Patent Application WO 03/097820

Patent reference 2: JP-A-2001-11090

DISCLOSURE OF THE INVENTION

Problems that the Invention is to Solve

When starch or sucrose is ingested, starch or sucrose is digested and absorbed to cause a rapid increase of blood glucose level (blood glucose concentration). The increase of blood glucose level in healthy normal humans stimulates insulin secretion, so that blood insulin concentration is increased to enhance the action of promoting sugar utilization and then, blood glucose level is decreased. In such manner, blood glucose level is adjusted. About 15 minutes after healthy normal humans ingest starch or sucrose, the blood glucose level reaches the highest in arteries. About 30 minutes after healthy normal humans ingest starch or sucrose, the blood glucose level reaches the highest in veins. Subsequently, the blood glucose levels gradually resume the individual normal levels. Sucrose is highly digested and absorbed so sucrose is useful as a carbohydrate excellent for children's growth or as a food taken when humans feel tired. Because sucrose increases blood glucose level so rapidly to stimulate insulin secretion, sucrose is regarded as a cause of obesity. Additionally, patients with diabetes mellitus are under controls of the intake of sucrose. When starch or sucrose is ingested too much due to too much food intake or too much drinking, the amount of glucose to be processed is increased in blood. Thus, the amount of insulin secreted from pancreas is increased. When such state is sustained for a long term, the pancreas function is deteriorated and exhausted, to cause the onset of diabetes mellitus. When a human subject falls into obesity, the amount of insulin required is increased, to cause the deterioration of the pancreas function. When the pancreas is exhausted to cause the deterioration thereof, insulin falls into insufficiency, so that sugar never processed is excreted into urine. So as to prevent the occurrence of such state, importantly, pancreas should not be exhausted, i.e. insulin secretion should not be stimulated with a rapid, too much increase of blood glucose level. Such important aspects should be rigidly followed for dietary therapy of patients with diabetes mellitus.

In accordance with the invention, it is provided a novel use of D-psicose (the use for suppressing the abnormal intra-day increase of blood glucose level).

In accordance with the invention, more specifically, it is provided a technique for using D-psicose capable of suppressing the abnormal intra-day increase of plasma glucose concentration, by simply incorporating or orally administering D-psicose in foods or drinks in forms of sweeteners, seasonings, food additives, food materials, foods and drinks, health food and drink products, pharmaceutical products and feeds.

In case of a food, for example, it is an object of the invention to provide a composition and a method for suppressing the abnormal increase of plasma glucose level, by simply allowing D-psicose to be mixed into common diets for ingestion.

Means for Solving the Problems

The invention comprises a composition for suppressing the abnormal intra-day increase of plasma glucose concentration (blood glucose level), as described below in (1) through (11).
(1) A composition for suppressing the abnormal intra-day increase of plasma glucose concentration (blood glucose level), which contains D-psicose as the active component.
(2) A composition for suppressing the abnormal intra-day increase of plasma glucose concentration (blood glucose level) as described above in (1), which is a composition in blend with D-psicose and/or a derivative thereof.
(3) A composition for suppressing the abnormal intra-day increase of plasma glucose concentration (blood glucose level) as described above in (1) or (2), which is a mixture of D-psicose and D-fructose.
(4) A composition for suppressing the abnormal intra-day increase of plasma glucose concentration (blood glucose level) as described above in (3), where the mixture is a crystalline mixture.
(5) A composition for suppressing the abnormal intra-day increase as described above in any one of (1) through (4), where D-psicose and/or a derivative thereof is blended in the composition to a content of 0.1 to 50% by weight.
(6) A composition for suppressing the abnormal intra-day increase of plasma glucose concentration (blood glucose level) as described above in any one of (1) through (5), where the composition is in a form selected from the group consisting of sweeteners, seasonings, food additives, food materials, health food and drink products, pharmaceutical products and feeds and blended with D-psicose and/or a derivative thereof as the active component.
(7) A composition for suppressing the abnormal intra-day increase of plasma glucose concentration (blood glucose level) as described above in (6), where D-psicose and/or a derivative thereof is blended in a food containing carbohydrates and/or sugars to a content of 0.1 to 50% by weight of the total carbohydrate amount (total sugar amount) in the food.
(8) A composition for suppressing the abnormal intra-day increase of plasma glucose concentration (blood glucose level) as described above in (6), where D-psicose and/or a derivative thereof is blended in a drinkable liquid such as water to a content of 0.1 to 50% by weight.
(9) A composition for suppressing the abnormal intra-day increase of plasma glucose concentration (blood glucose level) as described above in (6), where D-psicose and/or a derivative thereof is blended in a feed containing carbohydrates and/or sugars to a content of 0.1 to 50% by weight of the total carbohydrate amount (total sugar amount) in the feed.
(10) A composition for suppressing the abnormal intra-day increase of plasma glucose concentration (blood glucose level) as described above in (6), where the health food and drink products are food and drink products for diets or diabetic diets.
(11) A composition for suppressing the abnormal intra-day increase of plasma glucose concentration (blood glucose level) as described above in (10), where the diabetic diets are diets for diabetes mellitus, having effects on saving insufficient insulin, ameliorating insulin sensitivity, and ameliorating hyperglycemia, as based on the D-psicose action.

In accordance with the invention, methods for using D-psicose as described below in (12) through (18) are provided.
(12) A method for using D-psicose in suppressing the abnormal intra-day increase of plasma glucose concentration (blood glucose level), comprising giving D-psicose at given times to suppress the abnormal increase of plasma glucose concentration throughout the day.
(13) A method for using D-psicose in suppressing the abnormal intra-day increase of plasma glucose concentration (blood glucose level) as described above in (12), where the action of D-psicose to suppress the abnormal intra-day increase of plasma glucose concentration is based on an action of enhancing the uptake of blood glucose into liver and muscle, and/or an action of inhibiting sugar digestive enzymes in the gastrointestinal tract, and/or an action of inhibiting sugar absorption from the gastrointestinal tract, and/or an action of stimulating insulin secretion from pancreas.
(14) A method for using D-psicose as described above in (12) or (13), where D-psicose is D-psicose and/or a derivative thereof, and/or is in a form of a composition in blend with D-psicose and/or a derivative thereof.
(15) A method for using D-psicose as described above in any one of (12) through (14), where D-psicose and/or a derivative thereof is blended in the composition to a content of 0.1 to 50% by weight.
(16) A method for using D-psicose as described above in (15), where D-psicose and/or a derivative thereof is blended in a food containing carbohydrates and/or sugars to a content of 0.1 to 50% by weight of the total carbohydrate amount (total sugar amount) in the food.
(17) A method for using D-psicose as described above in (15), where D-psicose and/or a derivative thereof is blended in a drinkable liquid such as water to a content of 0.1 to 50% by weight.
(18) A method for using D-psicose as described above in (15), where D-psicose and/or a derivative thereof is blended in a feed containing carbohydrates and/or sugars to a content of 0.1 to 50% by weight of the total carbohydrate amount (total sugar amount) in the feed.

Advantages of the Invention

In accordance with the invention, a novel use of D-psicose in suppressing the intra-day variation of plasma glucose concentration can be provided.

In accordance with the invention, it is provided a method for using D-psicose in suppressing the abnormal intra-day increase of plasma glucose concentration comprising simply incorporating or orally administering D-psicose in foods or drinks in forms of sweeteners, seasonings, food additives, food materials, food and drink products, health food and drink products, pharmaceutical products, and feeds. In accordance with the invention, sweeteners, seasonings, food additives, food materials, food and drink products, health food and drink products, pharmaceutical products, and feeds can be provided, which can be used for preventing or therapeutically treating diseases requiring the saving of insufficient insulin, the amelioration of insulin sensitivity and the amelioration of hyperglycemia, and diseases of which the symptoms can be ameliorated via the suppression of the abnormal intra-day increase of plasma glucose concentration (blood glucose level) or of which the onset can be prevented via the suppression thereof, such as diabetes mellitus, occult diabetic states, obesity, hyperglycemia, and arteriosclerosis.

In case of foods, for example, the invention provides a method for suppressing the abnormal increase of plasma glucose concentration, by simply mixing D-psicose into a common diet for ingestion.

BEST MODE FOR CARRYING OUT THE INVENTION

Figure 1:
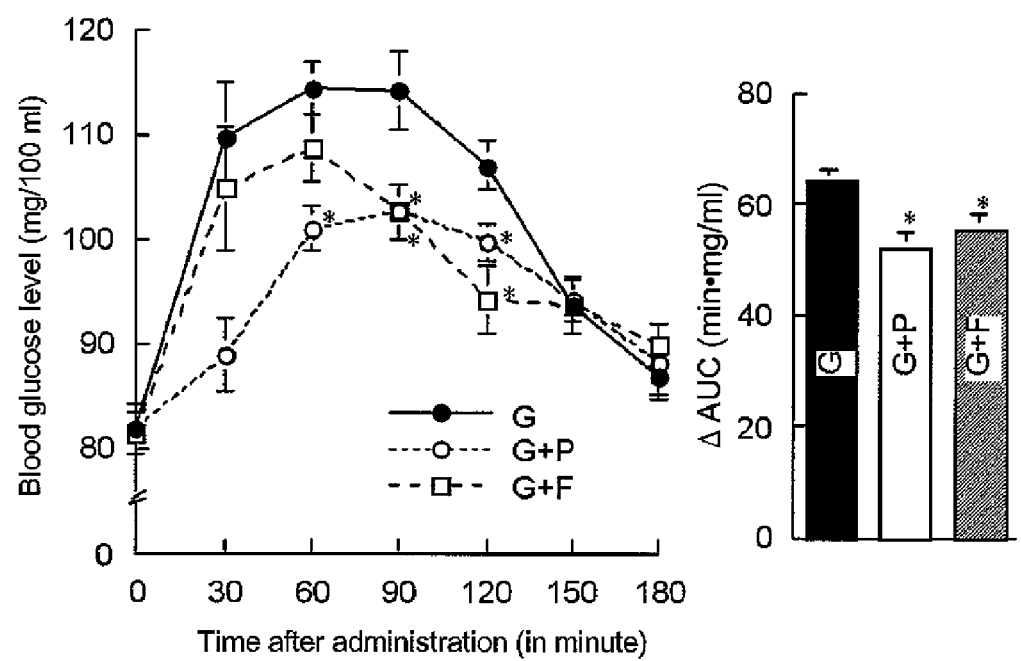
FIG. 1 shows the blood glucose levels in rats orally given 2.0 g/kg glucose (G), 2.0 g/kg glucose+0.32 g/kg psicose (G+P) and 2.0 g/kg glucose+0.32 g/kg fructose (G+F) as well as the increment of the area under the curve of the blood glucose levels (ΔAUC) in these rats. The data are shown in mean±standard deviation. *: significant difference at p<0.05 from G (according to one-dimensional variation analysis and the Fischer's OPLSD test).

The patent reference 1 includes the following description about the function of D-psicose to decrease the increased blood glucose.

It was verified about the action of D-psicose to promote insulin secretion that by supporting the action of D-psicose to mildly suppress blood glucose in an animal (rat), D-psicose had an action of decreasing blood glucose at hyperglycemia and an action to promote insulin secretion, and that D-psicose hardly saccharified protein.

Generally, diabetes mellitus is essentially the impairment of insulin secretion specific to glucose. Even in a case of the impairment of insulin secretion via glucose, the action of the ketohexose belonging to rare sugar may expectantly promote insulin secretion effectively. In such manner, it is elucidated that the ketohexose belonging to rare sugar has an action of stimulating insulin secretion from pancreas β cell and an action of enhancing insulin secretion at a hyperglycemic state. Thus, the ketohexose belonging to rare sugar may expectantly be a substance with a novel action mechanism never found.

Additionally, the ketohexose belonging to rare sugar may expectantly promote insulin secretion, in patients with diabetes mellitus and accordingly with clinically observed hyperglycemia to ameliorate blood glucose level.

Additionally because the ketohexose belonging to rare sugar after enteral administration suppresses glucose absorption and never has any influence on sugar metabolism, the ketohexose possibly suppresses post-meal hyperglycemia in diabetes mellitus and is therefore a substance advantageous for preventing or therapeutically treating diabetes mellitus.

Furthermore, the ketohexose belonging to rare sugar is observed to have an effect on preventing arteriosclerosis in a significant relation with diabetes mellitus and complications thereof. Since the main cause of death due to diabetes mellitus is an arteriosclerotic disease, the ketohexose belonging to rare sugar and having an additional action of suppressing arteriosclerosis is expectantly an innovative therapeutic agent of diabetes mellitus, which can ameliorate blood glucose level and prevent arteriosclerosis. Additionally, the ketohexose belonging to rare sugar may expectantly be a health supplementary food, possibly having such therapeutic effects and an anti-obesity effect.

Thus, the inventors further made investigations so as to obtain fundamental data about the involvement of D-psicose in sugar metabolism, by carrying out an oral glucose tolerance tests using rats. Further, the inventors made investigations about the influence of D-psicose on hepatic glycogen content. The inventors verified the action of D-psicose to increase hepatic glycogen content to suppress the increase of blood glucose level after oral glucose tolerance tests. Additionally, the inventors found an action of D-psicose to suppress daily blood glucose level to a lower level, not from the standpoint so far of suppressing the increase of blood glucose level.

Descriptions are now made about the action of D-psicose for enhancing the uptake of blood glucose into liver.

The action of enhancing the amount of liver glycogen, which involves the increase of liver protein amount, is also found in case of D-tagatose (Bar et al., Reg Toxicol Pharmacol 29: S11-S28 (1999); Bar A, Reg Toxicol Pharmacol 29: S83-S93 (1999); Boesch et al., Reg Toxicol Pharmacol 33: 257-267 (2001)). Bar et al. report (Bar et al., Reg Toxicol Pharmacol 29: S11-S28 (1999)) that the action of D-tagatose as described above never involves any histological change of liver. Additionally because not any toxicity of D-psicose to cause the deterioration of liver functions has yet been verified (Matsuo et al., J Nutr Sci Vitaminol 48: 512-516 (2002)), the action of D-psicose on liver may be identical to that of D-tagatose.

The stimulation of insulin secretion from pancreas with D-psicose is now described below.

When ingested, starch or sucrose is digested and absorbed to cause a rapid increase of blood glucose level (blood glucose concentration). In a healthy normal human subject, the increase of blood glucose level stimulates insulin secretion, leading to an increase of blood insulin concentration and the enhancement of an action of promoting the utilization of sugar, which subsequently works to decrease blood glucose level. In such manner, blood glucose level is adjusted. In healthy normal humans, starch or sucrose ingested makes the blood glucose level reach the maximum about 15 minutes and about 30 minutes later in arteries and veins, respectively. Gradually, then, the blood glucose levels resume the normal levels.

D-Psicose has an action of suppressing a rapid increase of blood glucose level via D-glucose composing digestive sugars incorporated. When D-psicose is ingested together with digestive sugars (carbohydrates and/or sugars) decomposed and absorbed in the gastrointestinal tract, such as sucrose, starch and oligosaccharides derived from starch, D-psicose exerts the action of appropriately suppressing the increase of blood glucose level when D-psicose is blended in an amount within a range of 0.1 to 50% by weight of the total amount of carbohydrates (the total amount of sugars) ingested.

The action of D-psicose for inhibiting sugar digestive enzymes in the gastrointestinal tract is now described below.

Starch and sucrose occupy 80 to 90% of total carbohydrates ingested by humans. Sucrose reaches the small intestine without any intermediate decomposition in the gastrointestinal tract, while starch is decomposed into α-dextrin with α-amylase in saliva, which then reaches the stomach and then reaches the duodenum, where α-dextrin is hydrolyzed into maltodextrin and then into maltose and isomaltose, with α-amylase secreted from pancreas. Such sugars having reached the small intestine are then decomposed into monosaccharides as composing sugars with α-glucosidase locally existing in the villus of the small intestine. Specifically, maltose and malto-oligosaccharides are individually decomposed into monosaccharides with maltase, while isomaltose and sucrose are also individually decomposed into monosaccharides with a complex enzyme isomaltase/sucrase.

When D-psicose and a mixture of D-fructose and D-psicose (psico-rare sugar) are individually administered concurrently with sucrose, the increase of blood glucose level up to 60 minutes after the administration can be suppressed, compared with the single administration of sucrose. D-Psicose and psico-rare sugar may possibly have an action of inhibiting sucrase. The action is at a level almost equal to that of L-arabinose, of which the sucrase-inhibiting action has been verified.

At enzyme activity-inhibiting experiments, the activity level of an enzyme decomposing polysaccharides varies significantly, depending on the method for assaying the activity. Because the resulting products have a reducing activity, such enzyme is assayed by the Somogyi-Nelson method. When a product is D-glucose, the product is assayed with glucose oxidase as a specific sensor. However, the glucose oxidase method may sometimes be reactive with sugars other than D-glucose. Therefore, the assay results are generally variable. When the enzyme is of an exo-type (the enzyme decomposes polysaccharides sequentially from the end thereof), the reaction generally produces monosaccharides or oligosaccharides. In case of an endo-type (the enzyme decomposes polysaccharides randomly), the reaction produces products such as oligosaccharides and large polysaccharides. By assaying the reducing activities of these products, the enzyme activity can be assayed. The reducing activity of a product sometimes varies, depending on the molecular weight of the product, as described above. Therefore, the resulting assayed activity may be inconstant. The experimental results show that such inhibiting activity was observed under the described conditions. Compared with the assay results of existing inhibiting substances such as L-arabinose as controls under the same conditions, discussion can be done.

A quantitative assay when established in future will elucidate the mechanism of the inhibition. It is suggested that the mechanism of L-arabinose to inhibit invertase is a non-antagonistic inhibition where L-arabinose attacks an enzyme part different from the activity center. It is unknown whether or not the same inhibiting activity when exerted may have the same mechanisms as that of L-arabinose. Therefore, currently, only a semi-quantitative assay result can be obtained, which corresponds to the comparison of inhibition at a given concentration.

Concerning the inhibition results of various hydrolases, the inhibition of glucoamylase is a very important result although the inhibition thereof never actually works in animal intestine. This is not due to the simple reason that enzymes generated by enterobacteria exist concurrently. In research works so far, there have not been used monosaccharides, particularly rare sugar. The inhibition of various hydrolases with various types of rare sugar has never been examined systematically so far but is now verified and the inhibiting activity of rare sugar works within a considerably wide range. Significantly, these are very important results. The inhibition of various hydrolases with rare sugar has at least led to the potential elucidation of the intra-day variation mechanism. In future, the control of hydrolases with rare sugar and the development of a technique for applying such rare sugar will be highly possibly established. For example, any inhibition of the decomposition of polysaccharides in the natural kingdom may lead to a possibility of the storage of polysaccharides.

The suppression of the abnormal intra-day increase of plasma glucose concentration (blood glucose level) is now described below. The intra-day variation of blood glucose level normally occurs. The suppression thereof means the suppression of the abnormal increase of plasma glucose concentration throughout the day.

When feeds with D-psicose and psico-rare sugar added thereto at 5% were given to rats at given times, the plasma glucose concentration in the rats was variable at low levels throughout the day. This indicates a possibility of suppressing the increase of blood glucose level when D-psicose and psico-rare sugar were added to daily diets. As clearly demonstrated in the research works so far, D-psicose was at the zero energy value. Doubtfully, the suppression of plasma glucose concentration with D-psicose and psico-rare sugar may be ascribed to a simple reduction of the sugar intake. However, no difference in the intra-day variation of plasma glucose concentration was observed between the D-psicose group and the psico-rare sugar group (fructose:psicose=3:1) ingesting D-psicose only ¼-fold that in the D-psicose group. Accordingly, the suppression thereof cannot be explained, only on the basis of the sugar intake. Alternatively, the mechanism of the suppression of the blood glucose level increase with D-psicose has not yet been characterized. Therefore, an unknown function never anticipated may possibly exist.

The discovery of the action of suppressing the abnormal intra-day increase of blood glucose level is a new fruitful outcome. The action works for suppressing such abnormal increase while suppressing daily blood glucose level at a low level, not from the standpoint so far of the suppression of the increase of blood glucose level. Apparently, the suppression is a phenomenon occurring in a long-term administration. We are now under way of experiments so as to determine how long the administration should be continued to induce the emergence of the phenomenon. Further, experiments are required so as to verify the possibility that "such phenomenon never occurs" as observed before the administration when the administration is terminated.

Additionally, the body weight increase for a while in an early stage of the D-psicose administration is more or less small compared with controls, but the body weight increase follows the same pattern as that of the controls. This may be due to the suppression of sugar absorption. However, it may mean that the occurrence of such intra-day variation requires a considerable time.

Derivatives of D-psicose are now described hereinbelow. Compounds resulting from a chemical reaction to modify the molecular structure of a starting compound are referred to as derivatives of the starting compound. Derivatives of hexoses including D-psicose are generally sugar alcohols (when a monosaccharide is reduced, the aldehyde group and the ketone group in the monosaccharide are modified into alcohol group, so that the monosaccharide is modified into a polyhydric alcohol with the same alcoholic group number as the number of carbon atoms), uronic acid (resulting from the oxidation of the alcohol group in monosaccharides and including known, naturally occurring D-glucuronic acid, galactouronic acid and mannuronic acid), and amino sugar (resulting from the substitution of the OH groups in sugar molecules with NH2 group and including glucosamine, chondrosamine and glycoside). However, the derivatives are not limited to them.

The invention relates to sweeteners, seasonings, food additives, food materials, foods and drinks, health food and drink products, pharmaceutical products and feeds, for use in preventing and therapeutically treating diseases requiring the saving of insufficient insulin, the amelioration of insulin sensitivity and the amelioration of hyperglycemia, and diseases of which the symptoms can be ameliorated via the suppression of the abnormal intra-day increase of plasma glucose concentration (blood glucose level) or of which the onset can be prevented via the suppression thereof, such as diabetes mellitus, occult diabetic states, obesity, hyperglycemia, and arteriosclerosis.

The sweeteners, seasonings, food additives, food materials, foods and drinks, health food and drink products, pharmaceutical products and feeds in accordance with the invention contain a composition in blend with D-psicose and/or a derivative thereof, and/or a mixture of D-psicose and a derivative thereof as the active component.

As the mixture of D-psicose, a crystalline sugar complex containing D-psicose and D-fructose as developed so far is now described (see the official gazette of JP-A-2001-11090).

So as to produce such mixture sugar, advantageously, D-ketohexose.3-epimerase reacts with D-fructose for epimerization, for preparing a mixture of D-psicose and D-fructose. The ratio of D-psicose and D-fructose in the resulting sugar is generally about 20 to 25% and about 80 to 75%, respectively per solids. If necessary, the mixture sugar of D-psicose and D-fructose at the ratio may optionally be produced by reacting D-ketohexose.3-epimerase with D-psicose. Using an inorganic and/or organic catalyst, D-fructose may be epimerized to produce a mixture of D-psicose and D-fructose. In that case, generally, the purity of D-psicose is low. Therefore, D-psicose may possibly be added to the resulting product, or D-fructose may be removed from the product by solvent partition, membrane separation, column fractionation, yeast treatment and enzymatic treatment, to raise the purity of the resulting D-psicose. It is needless to say that D-psicose and D-fructose may be blended together at an appropriate ratio, to prepare a mixture of D-psicose and D-fructose.

From a sugar solution containing D-psicose and D-fructose, a crystalline sugar complex containing D-psicose and D-fructose is generated and collected, to produce a crystalline sugar complex containing D-psicose and D-fructose. The process may comprise charging a sugar containing D-psicose and D-fructose, desirably a high concentration solution of a composition ratio of D-psicose and D-fructose at about 1:2 to about 1:4, more desirably an aqueous solution at a solid concentration of 70 to 98 w/w % in for example a crystallization can, then charging a crystalline sugar complex containing D-psicose and D-fructose at an appropriate amount, desirably at about 0.01 to 10% as a seed crystal therein, mixing the resulting mixture together for crystallization to prepare a maskit, and then pulverizing the resulting maskit to collect the resulting powder. In this case, a hydrophilic organic solvent such as ethanol may be added to the sugar solution containing D-psicose and D-fructose, to promote the generation of the crystalline sugar complex containing D-psicose and D-fructose.

The development of foods and sweeteners stating efficacies for diabetes mellitus and diets has been accomplished, where digestive sugars such as common sucrose, starch and oligosaccharides derived from starch are mixed with D-psicose alone or with a mixture of D-fructose and D-psicose.

In other words, foods increasing post-meal blood glucose level include foods containing starch at a high content. Compositions in blend with D-psicose and/or a derivative thereof and/or a mixture of D-psicose and a derivative thereof can be utilized as food materials suppressing a rapid increase of post-meal blood glucose level in the foods described above.

For example, an application of D-psicose as a sweetener is described below. In case that the crystal and syrup of D-psicose and a crystalline sugar complex of D-psicose and D-fructose are used as sweeteners, for example, these may be mixed and used with one or two or more of other sweeteners such as powdery candy, glucose, maltose, isomerized sugar, sucrose, trehalose, honeybee, maple sugar, sorbitol, xylitol, lactitol, maltitol, dihydrochalcone, stevioside, α-glycosyl-stevioside, Momordica grosvenori Swingle (luohangus in Chinese) sweets, glycyrrhizin, L-aspartyl-L-phenylalanine methyl ester, saccharin, glycine and alanine. Additionally, these may be mixed and used with fillers such as dextrin, starch and lactose. These may be used as they are or these may be mixed with for example fillers, excipients, and binders to be molded into granules, spheres, tablets, bars, plates and cubes for use.

D-Psicose has refined and refreshing sweetness without any unpleasant taste accompanied by bitterness and astringency and has a sweetness type rather similar to the sweetness of D-fructose. The sweetness degree of D-psicose is about 70% of that of sucrose. The sweetness of D-psicose and the crystalline sugar complex containing D-psicose and D-fructose harmonizes well with other tastes of various substances, including acid taste, salty taste, astringency, uma-mi and bitterness. Therefore, the sweetness thereof can be used advantageously in giving sweetness to common general foods and drinks or modifying the taste thereof, or modifying the quality thereof.

These may be used as a sweetener for various seasonings for example soy sauce, powdery soy sauce, miso (soybean) paste, powdery miso paste, moromi (unrefined sake), hi-shio (fermented food products or sauces called "jyan" in Chinese), seasoned powders for sprinkling over rice, mayonnaise, dressings, edible vinegar, seasoned vinegar, powdery vinegar for vinegar-seasoned rice (sushi in Japanese), Chinese seasoning, tempura dipping sauce, noodle dipping sauce, sauce, ketchup, gravy for broiled meat, curry roux, stew sauce, soup seasoning sauce, Japanese soup seasoning sauce, complex seasonings, mirin (sweet sake), new mirin, table sugar, and coffee sugar. These may also be used advantageously as for example taste modifiers and quality modifiers.

Additionally, these may be used as sweeteners for various foods and drinks, including various Japanese sweets such as rice crackers, small rice crackers (arare), rice cracker sweets (okoshi), steamed rice cakes (mochi), buns with bean-jam fillings, steamed rice cake sweets (u-iro), bean-jam fillings, bean-jam cakes in rectangular shapes, watery bean-jam cakes, kingyoku (agar sweet with sugar), jelly, sponge cake (castella), and sweet candies; various cakes and pastries such as bread, biscuits, crackers, cookies, pies, puddings, butter cream, cream puff, waffle, sponge cake, doughnut, chocolate, chewing gum, caramel, and candy; icy sweets such as ice cream and sherbets; syrups such as fruit immersed in syrups and ice honeybee; pastes such as flower paste, peanut paste and fruit paste; processed foods of fruits and vegetables, for example jam, marmalade, syrup-immersed food products, and sugar confectioneries; cereal-processed foods such as breads, noodles, rice menus, and artificial meat; pickles such as fukujin-zuke (various vegetables immersed in specific seasoned liquids), bettara-zuke (Japanese radish pickles prepared by sprinkling seasoned powders), senmai-zuke (very thin sliced Japanese radish pickles prepared by sprinkling seasoned powders), and rakkyo-zuke (Japanese garlic pickles prepared by dipping Japanese garlic in specific seasoned liquids); seasonings for pickles, such as seasonings for takuan-zuke (Japanese radish pickles prepared by sprinkling specific powders containing rice bran over the radish) and seasonings for hakusai-zuke (Chinese cabbage pickles); meat products such as ham and sausage; fish meat products such as fish ham, fish sausage, fish cake, hollowed fish cake, and fish tempura; various delicate tidbits such as sea urchin, salty and seasoned squid, vinegar-seasoned seaweed, sliced and dried squid in pieces, and sweet sake-dipped and then dried fugu (blowfish); seasoned and boiled pickles produced from seaweed, mountain plants, dried squid, small fishes and shellfishes; everyday dishes such as boiled beans, potato salad, and cooked seaweed in a roll shape; bottled products and canned products of dairy products, fish, meat, fruits and vegetables; alcoholic drinks and liqueurs such as synthetic alcoholic drinks, fruit drinks, western wines and liqueurs; refreshing drinks such as coffee, cocoa, juice, carbonate drinks, lactic acid drinks, and lactic acid bacteria drinks; premix powders such as pudding mix and hotcake mix; and instant drinks such as instant juice, instant coffee, instant bean juice, and instant soup. Additionally, these may advantageously be used as taste modifiers and quality modifiers.

A composition in blend with D-psicose and/or a derivative thereof and/or a mixture of D-psicose and a derivative thereof may be used in foods slightly requiring sweetness, such as Chinese noodle (ramen), noodles, Japanese noodle as prepared by using wheat flour and starch, and mush potato, salad and croquette as prepared by using potato as the main raw material. When D-psicose is mixed at 1 to 5% of the total carbohydrate amount (total sugar amount) in these foods for cooking, the resulting foods are not sweet or very slightly sweet at such mixing ratio because these materials are at a sweetness degree lower than that of sucrose. Further, the resulting foods suppress a rapid increase of blood glucose level and also suppress insulin secretion to a lower level.

Additionally, the composition may also be used for the same purpose for confectioneries and breads slightly requiring sweetness, which are prepared by using wheat flour, starch and rice powder as main raw materials. As described above, a composition in blend with D-psicose and/or a derivative thereof and/or a mixture of D-psicose and a derivative thereof may be used at an amount within a very wide range.

The health food and drink products or foods and drinks for patients with diabetes mellitus in accordance with the invention contain a composition in blend with D-psicose and/or a derivative thereof and/or a mixture of D-psicose and a derivative thereof in accordance with the invention as the active component. Additionally, the health food and drink products or foods and drinks for patients with diabetes mellitus in accordance with the invention contain the composition to a D-psicose content of 0.1 to 50% by weight of the total carbohydrate amount (total sugar amount) in the food and drink products or in the foods and drinks. When normal healthy humans or patients with diabetes mellitus ingest the health food and drink products or the foods and drinks for patients with diabetes mellitus, D-psicose with no influence on the sugar metabolism suppresses the decomposition with α-glucosidase localized in the villus of the small intestine into monosaccharides as composing sugar and also suppresses glucose absorption, so that the rapid increase of blood glucose level via D-glucose can be suppressed.

Additionally, the foods and drinks for diets in accordance with the invention contain a composition in blend with D-psicose and/or a derivative thereof and/or a mixture of D-psicose and a derivative thereof in accordance with the invention as the active component. Additionally, the foods and drinks for diets in accordance with the invention contain the composition to a D-psicose content of 0.1 to 50% by weight of the total carbohydrate amount (total sugar amount) in the foods and drinks. When the foods and drinks for diets in accordance with the invention are ingested, D-psicose with no influence on sugar metabolism suppresses the decomposition with α-glucosidase localized in the villus of the small intestine into monosaccharides as composing sugars and also suppresses glucose absorption, so that the disposition toward obesity can be suppressed.

Furthermore, a pharmaceutical product and a prophylactic pharmaceutical agent enhancing glycogen synthesis and storage in liver to lower the reaction to increase blood glucose level can be provided, even when common foods and drinks are ingested (under a reduced control of dietary restriction).

The present inventor made an experiment in an experimental animal about the action of D-psicose to suppress the increase of blood glucose after an oral glucose tolerance test. The inventor verified the action of D-psicose to increase hepatic glycogen content and the action thereof to suppress the increase of blood glucose level after the oral glucose tolerance test.

By orally administering a pharmaceutical agent containing D-psicose or a derivative thereof as the active component, the action of D-psicose to enhance hepatic glycogen content to suppress the reaction of increasing blood glucose level can be utilized. Therefore, a pharmaceutical product (a prophylactic pharmaceutical agent or a therapeutic agent) suppressing a rapid increase of blood glucose level via D-glucose composing digestive sugars ingested at meals can be provided. Such prophylactic pharmaceutical agent or therapeutic agent is singly used for such purpose. Besides, these agents may be blended with appropriate additives such as general excipients, stabilizers, preservatives, binders, and disintegrators, formulated into an appropriate dosage form selected from for example liquids, capsules, granules, pills, powders, and tablets, and then orally or parenterally administered. For oral dosing, the dose is 0.3 to 50 g of D-psicose per day. Depending on the age and the symptoms, the dose may appropriately be raised or reduced. Preferably, the agent for suppressing the increase of blood glucose in accordance with the invention may be administered once daily or may be administered at an appropriate interval in dividend doses, such as twice or thrice daily, pre-meal or post-meal or in meal.

The feeds of the invention are feeds for cattle, chicken, and other feeding animals such as bee, silkworm and fish, and comprise a composition in blend with D-psicose and/or a derivative thereof and/or a mixture of D-psicose and a derivative thereof in accordance with the invention to a D-psicose content of 0.1 to 50% by weight of the total carbohydrate amount (total sugar amount) in the feeds. When such feeds are given to cattle, chicken, and other feeding animals such as bee, silkworm and fish, the tendency toward obesity can be reduced. Thus, the feeds of the invention are feeds useful for preventing pet obesity, preventing diabetes mellitus in pets, and obtaining edible meat with less fat.

A method for allowing sweeteners, seasonings, food additives, food materials, foods and drinks, health food and drink products, pharmaceutical products and feeds to contain a composition in blend with d-psicose and/or a derivative thereof and/or a mixture of D-psicose and a derivative thereof as described above may comprise charging D-psicose at 0.1% by weight or more, preferably 0.5% by weight or more in a process before the completion of the products, which process is selected appropriately from known processes such as mixing, kneading, dissolution, melting, immersion, permeation, sprinkling, coating, covering, spraying, injection, crystallization and solidification.

In a composition in blend with D-psicose, and/or a derivative thereof and/or a mixture of D-psicose and a derivative thereof in accordance with the invention, D-psicose is blended to 0.1 to 50% by weight of the composition. Preferably, the content is 0.5 to 30% by weight. More preferably, the content is 1 to 10% by weight. When D-psicose is at an amount less than 0.1% by weight in the composition, the action of D-psicose to suppress the abnormal intra-day increase of blood glucose level is insufficient. D-psicose at an amount more than 50% by weight in the composition is not preferable from the economical standpoint.

The invention is now described in detail in the following Examples. However, the invention is never limited by these Examples.

Example 1

Experiment 1

Influence of D-Psicose on the Reaction of Increasing Blood Glucose

Male Wistar rats of age 6 months were fed ad libitum under a condition that the bright cycle was at a temperature of 25° C. and a humidity of 50 to 70% from 8:00 am to 20:00 pm, for preliminary feeding for one week. On the day before the experiment, the rats were fasted for 12 hours and subsequently orally given D-glucose at 2 g/kg (in the form of 50% glucose solution) using a probe. Blood was drawn before the dosing and 30, 60, 90, 120, 150 and 180 minutes after the dosing. Blood glucose level was measured with a blood glucose meter. Alternatively, D-fructose or D-psicose at 0.32 g/kg (at 16% of D-glucose) was simultaneously given with D-glucose at 2 g/kg. In the same manner, blood glucose level was measured. Based on the resulting blood glucose levels, the area under the curve of blood glucose level ($\Delta AUC$) was calculated.

Experiment 2

Influence of D-Psicose on Liver Weight and Composition

Twenty-four male Wistar rats of age 3 weeks were fed ad libitum under a condition that the bright cycle was at a temperature of 25° C. and a humidity of 50 to 70% from 8:00 am to 20:00 pm, for preliminary feeding for one week. Subsequently, the rats were divided into 4 groups, each group consisting of 6 rats. The groups were defined a high fat/D-psicose diet (HF-P) group; a high fat/cellulose diet (HF-C) group; a low fat/D-psicose diet (LF-P) group; and a low fat/cellulose diet (LF-C) group. 20% beef fat and 5% soybean oil were used to prepare the high fat diets. 5% soybean oil was used to prepare the low fat diets. 5% D-psicose or cellulose was added to the individual diets. The compositions of the experimental diets are shown in Table 1. These rats were fed these experimental diets and water ad libitum for 16 weeks. On the last day of the experiment, the rats were decapitated and sacrificed to death, from which liver, flounder muscle and intraperitoneal fat tissues were resected. Glycogen, neutral fat and protein were assayed in the liver, while glycogen content was assayed in the flounder muscle.

TABLE 1

| | Group[1] | | | |
|---|---|---|---|---|
| | HF-P | HF-C | LF-P | LF-C |
| | Components (g/kg) | | | |
| Casein | 255.0 | 255.0 | 255.0 | 255.0 |
| DL-Methionine | 4.0 | 4.0 | 4.0 | 4.0 |
| Corn starch | 260.5 | 260.5 | 460.5 | 460.5 |
| Sucrose | 120.0 | 120.0 | 120.0 | 120.0 |
| D-Psicose | 50.0 | — | 50.0 | — |
| Cellulose | — | 50.0 | — | 50.0 |
| Beef fat | 200.0 | 200.0 | — | — |
| Soybean oil | 50.0 | 50.0 | 50.0 | 50.0 |
| Mineral mixture[2] | 45.0 | 45.0 | 45.0 | 45.0 |
| Vitamin mixture[2] | 13.0 | 13.0 | 13.0 | 13.0 |
| Choline chloride | 2.5 | 2.5 | 2.5 | 2.5 |
| Hydroxybutyl toluene | 0.01 | 0.01 | 0.01 | 0.01 |

[1]HF: high fat; LF: low fat; P: D-psicose; C: cellulose
[2]According to the AIN 76 formulation

Results

Experiment 1

The blood glucose level in the rats given orally D-glucose was increased and reached a peak in 60 to 90 minutes after the administration. Then, the blood glucose level was decreased up to 180 minutes later (FIG. 1). In case of simultaneous administration of D-fructose or D-psicose at 16% of D-glucose, the increase of the blood glucose level was suppressed. Compared with D-fructose, D-psicose likely reduced the increasing rate of blood glucose level. Compared with single administration of D-glucose, the blood glucose level after the simultaneous administration of D-fructose was significantly low in 90 and 120 minutes after the administration. In case of D-psicose, the blood glucose level was significantly low in 60, 90 and 120 minutes after the administration (FIG. 1).

Compared with the single D-glucose administration, ΔAUC was significantly low when D-fructose or D-psicose was simultaneously administered (FIG. 1).

Experiment 2

No difference in the rat body weight increment, the intake energy level and the intake energy efficiency was observed among the individual groups (Table 2). Compared with the high fat diet groups, the liver weight was significantly large in the low fat groups. Further, the addition of D-psicose increased liver weight, irrespective of the fat content (Table 2). Compared with the high fat diet groups, the hepatic glycogen content was significantly large in the low fat diet groups. Additionally, the addition of D-psicose tended to increase hepatic glycogen content (Table 2). The liver protein content per unit weight was significantly small in the low fat diet groups compared with the high fat diet groups, while in contrast, the protein amount per liver was significantly large in the low fat diet groups. The addition of D-psicose significantly increased the protein content per liver (Table 2). The neutral fat content per liver was significantly large in the low fat diet groups compared with the high fat diet groups (Table 2). Alternatively, the weight of the flounder muscle and the glycogen content therein were not different in the individual groups (Table 2). The weight of intraperitoneal fat tissues was significantly low in the low fat diet groups compared with the high fat diet groups, while no influence of the addition of D-psicose was observed (Table 2).

TABLE 2

|  | HF-P | HF-C | LF-P | LF-C |
|---|---|---|---|---|
| Body weight |  |  |  |  |
| Initial body weight (g) | 82 ± 2 | 83 ± 2 | 82 ± 2 | 82 ± 1 |
| Final body weight (g) | 321 ± 10 | 319 ± 9 | 326 ± 6 | 342 ± 9 |
| Increment (g) | 239 ± 10 | 236 ± 9 | 244 ± 6 | 260 ± 9 |
| Energy intake (kcal/day) | 49 ± 2 | 48 ± 1 | 48 ± 1 | 51 ± 1 |
| Energy efficiency (mg/kcal) | 44 ± 1 | 44 ± 1 | 45 ± 1 | 46 ± 1 |
| Liver |  |  |  |  |
| Weight (g) | 9.5 ± 0.5*# | 8.3 ± 0.4* | 13.2 ± 0.3# | 11.8 ± 0.3 |
| Glycogen (mg/g) | 10.6 ± 2.6* | 7.2 ± 1.6* | 18.8 ± 3.0 | 16.8 ± 3.7 |
| Glycogen (mg/tissue) | 107 ± 30* | 63 ± 17* | 252 ± 43 | 199 ± 45 |
| Neutral fat (mg/g) | 65.0 ± 9.6 | 67.2 ± 4.4 | 79.7 ± 8.4 | 99.7 ± 21.8 |
| Neutral fat (g/tissue) | 0.6 ± 0.1 | 0.6 ± 0.1* | 1.0 ± 0.1 | 1.2 ± 0.3 |
| Protein (mg/g) | 212 ± 2* | 215 ± 3* | 197 ± 6 | 201 ± 3 |
| Protein (g/tissue) | 2.0 ± 0.1*# | 1 ± 0.1* | 2.6 ± 0.1# | 2.4 ± 0.1 |
| Flounder muscle |  |  |  |  |
| Weight (mg) | 210 ± 8 | 209 ± 3 | 209 ± 10 | 230 ± 15 |
| Glycogen (mg/g) | 3.6 ± 0.2 | 3.4 ± 0.3 | 3.6 ± 0.4 | 3.4 ± 0.5 |
| Glycogen (mg/tissue) | 0.7 ± 0.1 | 0.7 ± 0.1 | 0.7 ± 0.1 | 0.8 ± 0.1 |
| Weight of intraperitoneal fat tissues (g) | 27 ± 2* | 28 ± 1* | 23 ± 1 | 25 ± 1 |

Data shown in mean ± standard deviation.
*Significant difference at $p < 0.05$ from low fat diet groups.
Significant difference at $p < 0.05$ from cellulose diet groups (by two-dimensional variation analysis and Fischer's PLSD test).

<Discussion>

A series of experiments so far reported the increase of liver weight via the addition of D-psicose to feeds (Matsuo et al., Asia J Clin Nutr 10:233-237 (2001); Yoshitake Baba, the graduation report paper from Kagawa University, the Agricultural Department in 1999 (not published); Tomohiro Tanaka, the graduation report paper from Kagawa University, the Agricultural Department in 1999 (not published)). Particularly at an amount of D-psicose added up to 20% of the weight of the feeds, the liver weight per body weight tended to increase in a manner dependent on the amount (the graduation report paper from Kagawa University, the Agricultural Department in 2001 (not published)). At the present experiment under conditions of variable fat contents in feeds, the increase of liver weight via D-psicose was reproduced. Alternatively, the protein content per liver increased due to the addition of D-psicose, which indicates that D-psicose has an action of allowing liver tissues to fall into hypertrophy. The action also increases the glycogen content per liver, but the glycogen content per unit weight increases due to the addition of D-psicose. Therefore, it is not clear whether or not the hepatic hypertrophy due to D-psicose is an adaptation for increasing glycogen reserve.

The action of increasing hepatic glycogen content involving the increase of such liver protein amount is also observed with D-tagatose (Bar et al., Reg Toxicol Pharmacol 29: S11-S28 (1999); Bar A, Reg Toxicol Pharmacol 29: S83-S93 (1999); Boesch et al., Reg Toxicol Pharmacol 33:257-267 (2001)). Bar et al. (Bar et al., Reg Toxicol Pharmacol 29:S11-S28 (1999)) reported that these actions via D-tagatose never involved any histological change of liver. Since no toxicity of D-psicose causing the deterioration of the hepatic function is demonstrated (Matsuo et al., J Nutr Sci Vitaminol 48: 512-516 (2002)), the action of D-psicose on liver may possibly be similar to that of D-tagatose.

At an oral glucose tolerance test, alternatively, D-psicose and D-fructose suppressed the reaction of increasing blood glucose via D-glucose. Wolf et al. (Wolf et al., J Nutr 132: 1291-1223 (2002)) made a report telling about research works using diabetic rats (fatty Zucker rats) that D-fructose suppressed the reaction of increasing blood glucose via D-glucose and maltodextrin. Therefore, the present research works support the results of them. Wolf et al. (Wolf et al., J Nutr 132:1291-1223 (2002)) describe that the suppression might be caused by the increase of glucose uptake into liver due to the increase of the liver glycogen reserve. D-Fructose generates fructose 1-phosphate with fructokinase. Fructose 1-phosphate promotes the glucokinase activity, to thereby promote the reaction to generate glucose 6-phosphate from D-glucose to increase the synthesis of hepatic glycogen, as reported (Gilboe and Nuttall, Arch Biochem Biophys 219: 179-185 (1982)). It is highly possibly indicated that psicose 1-phosphate generated with fructokinase may have a similar action or a more potent action. Bar et al. (Bar et al., Reg Toxicol Pharmacol 29:S11-S28 (1999)) also anticipates that the increase of hepatic glycogen content via D-tagatose may be ascribed to tagatose 1-phosphate.

Figure 2:
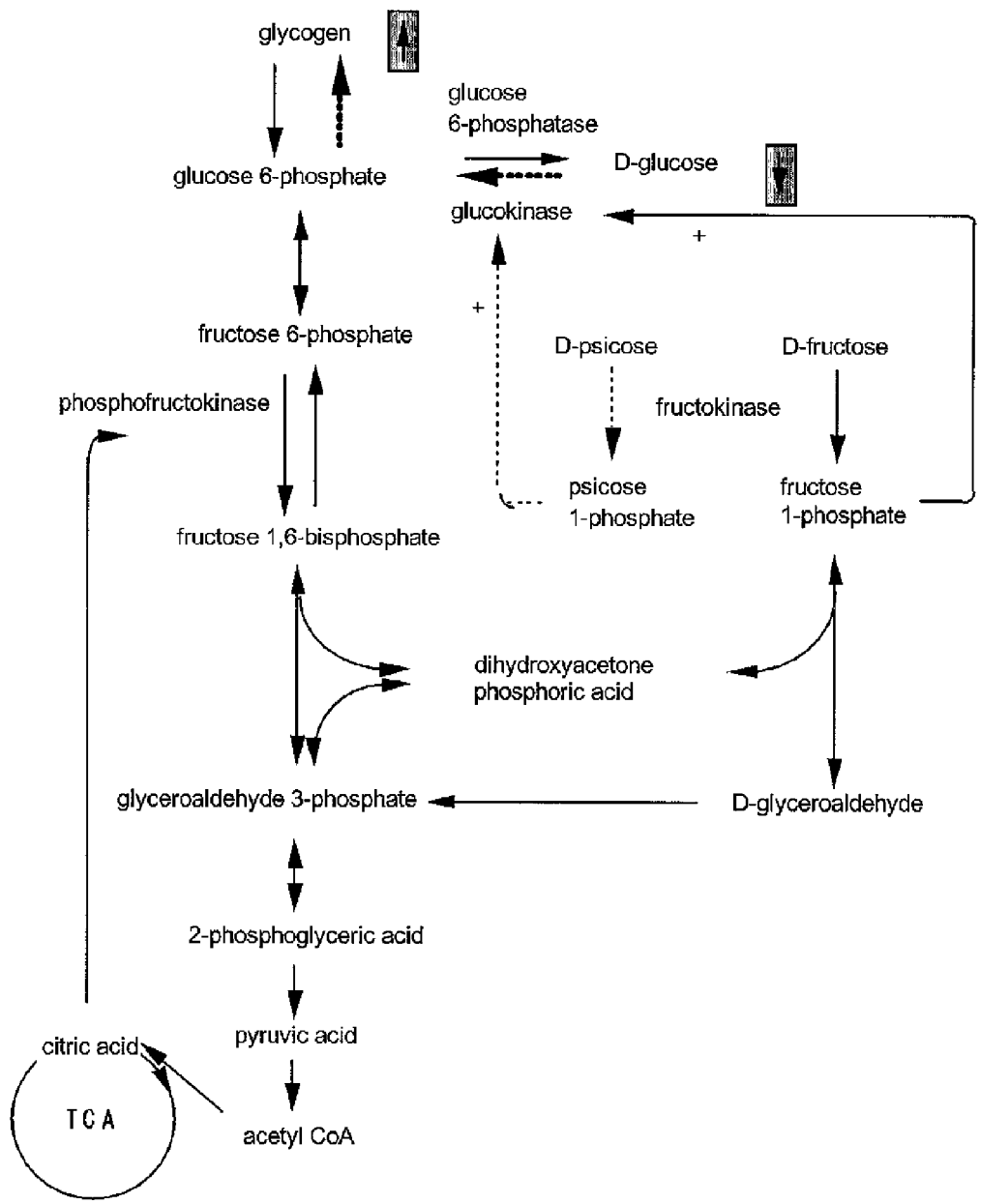
FIG. 2 shows the promotion of hepatic glycogen reserve with psicose and fructose (or a mixture of D-psicose and a derivative thereof) and the mechanism of suppressing the reaction of blood glucose.

It is believed that D-fructose has a potency of stimulating liver glycogen synthesis, which is lower than that of D-psicose. Unlike D-psicose, D-fructose itself may become a substrate for hepatic glycogen. It is interesting to know what kind of influence on blood glucose reaction or hepatic glycogen content a mixture of D-fructose and D-psicose has (FIG. 2). Because D-fructose bypasses the step with glycolytic phosphofructokinase, D-fructose is more rapidly metabolized than D-glucose (FIG. 2). It is believed that D-fructose or citric acid generated from the oxidation of fatty acid inhibits phosphofructokinase, to suppress glycolytic steps from glucose 6-phosphate and suppress glycogen decomposition (FIG. 2). Because the intake of a large amount of D-fructose promotes the synthesis of fatty acid, however, care should be taken in using a mixture of D-fructose and D-psicose in the same manner as in the case of using D-psicose alone.

The results of the present research works indicated that D-psicose enhanced the synthesis and reserve of glycogen in liver to reduce the reaction of increasing blood glucose level. It is now suggested that the mechanisms of them should be verified and a mixture of D-fructose and D-psicose should be examined in future.

Example 2

Actions of D-Psicose and a Mixture of D-Psicose and D-Fructose On the Inhibition of Sucrase and Maltase (In Vivo)

[Purpose]

It is known that D-psicose inhibits α-glucosidase in vitro. At the present experiment, the action will be verified. Additionally, it will be examined whether or not a mixture of D-psicose and D-fructose has an action of inhibiting sucrase and maltase.

Thirty-six male Wistar rats of age 6 months are divided into 6 groups. The following sugars were given to the rats in the individual groups after 12-hour fasting. Before the administration and 30, 60, 90, 120 and 180 minutes after the administration, blood is drawn from the tail vein, to assay plasma glucose and insulin concentration.

Experiment 1

1. Sucrose 2 g/kg (S)
2. Sucrose 2 g/kg+L-arabinose 200 mg/kg (SA)
3. Sucrose 2 g/kg+D-xylose 200 mg/kg (SX)
4. Sucrose 2 g/kg+D-fructose 200 mg/kg (SF)
5. Sucrose 2 g/kg+D-psicose 200 mg/kg (SP)
6. Sucrose 2 g/kg+(fructose 150 mg/kg+psicose 50 mg/kg) (SFP)

Experiment 2

1. Maltose 2 g/kg (M)
2. Maltose 2 g/kg+L-arabinose 200 mg/kg (MA)
3. Maltose 2 g/kg+D-xylose 200 mg/kg (MX)
4. Maltose 2 g/kg+D-fructose 200 mg/kg (MF)
5. Maltose 2 g/kg+D-psicose 200 mg/kg (MP)
6. Maltose 2 g/kg+(fructose 150 mg/kg+psicose 50 mg/kg) (MFP)

Experiment 3

1. Soluble starch 2 g/kg (SS)
2. Soluble starch 2 g/kg+L-arabinose 200 mg/kg (SSA)
3. Soluble starch 2 g/kg+D-xylose 200 mg/kg (SSX)
4. Soluble starch 2 g/kg+D-fructose 200 mg/kg (SSF)
5. Soluble starch 2 g/kg+D-psicose 200 mg/kg (SSP)
6. Soluble starch 2 g/kg+(fructose 150 mg/kg+psicose 50 mg/kg) (SSFP)

Figure 3:
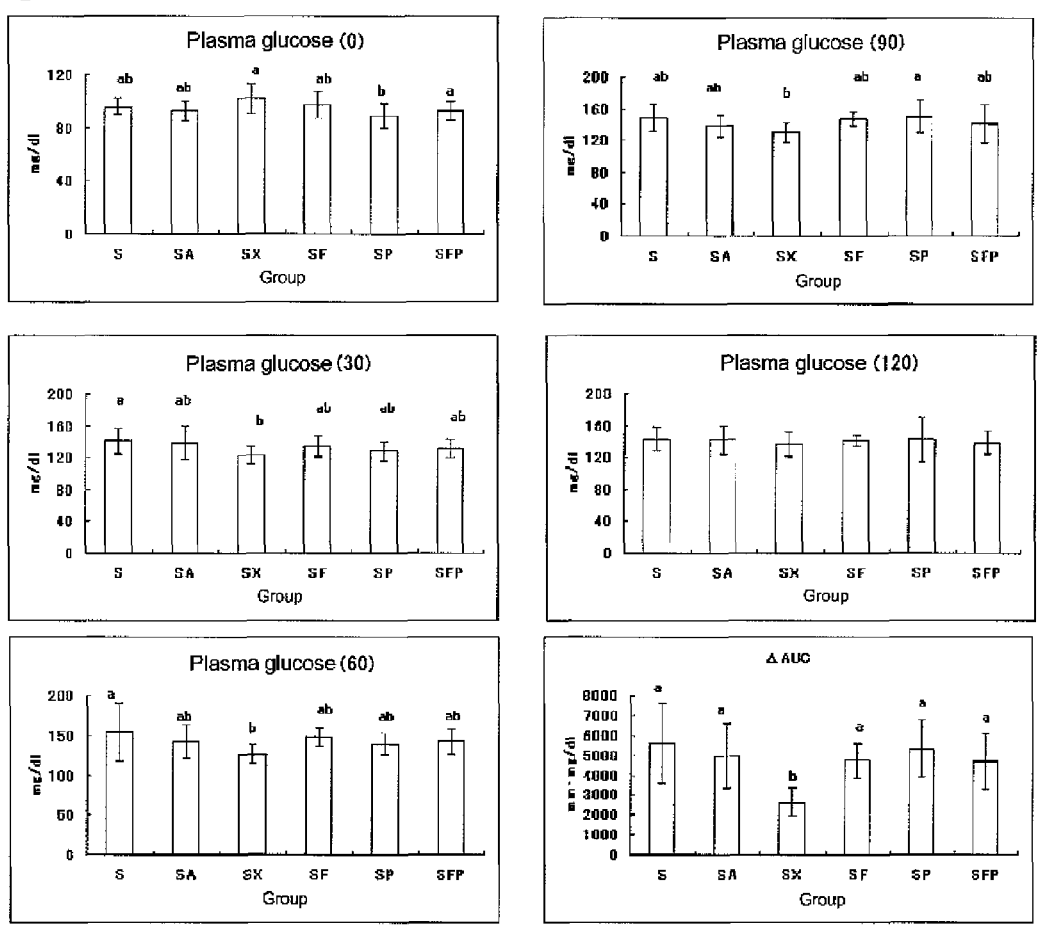
FIG. 3 shows the blood glucose levels 0, 30, 60, 90 and 120 minutes after sucrose (2.0 g/kg) (S), and 0.2 g/kg L-arabinose (A), D-xylose (X), D-fructose (F), D-psicose (P) and psico-rare sugar (FP) added to the sucrose were given, together with the increment of the area under the curve.
Figure 5:
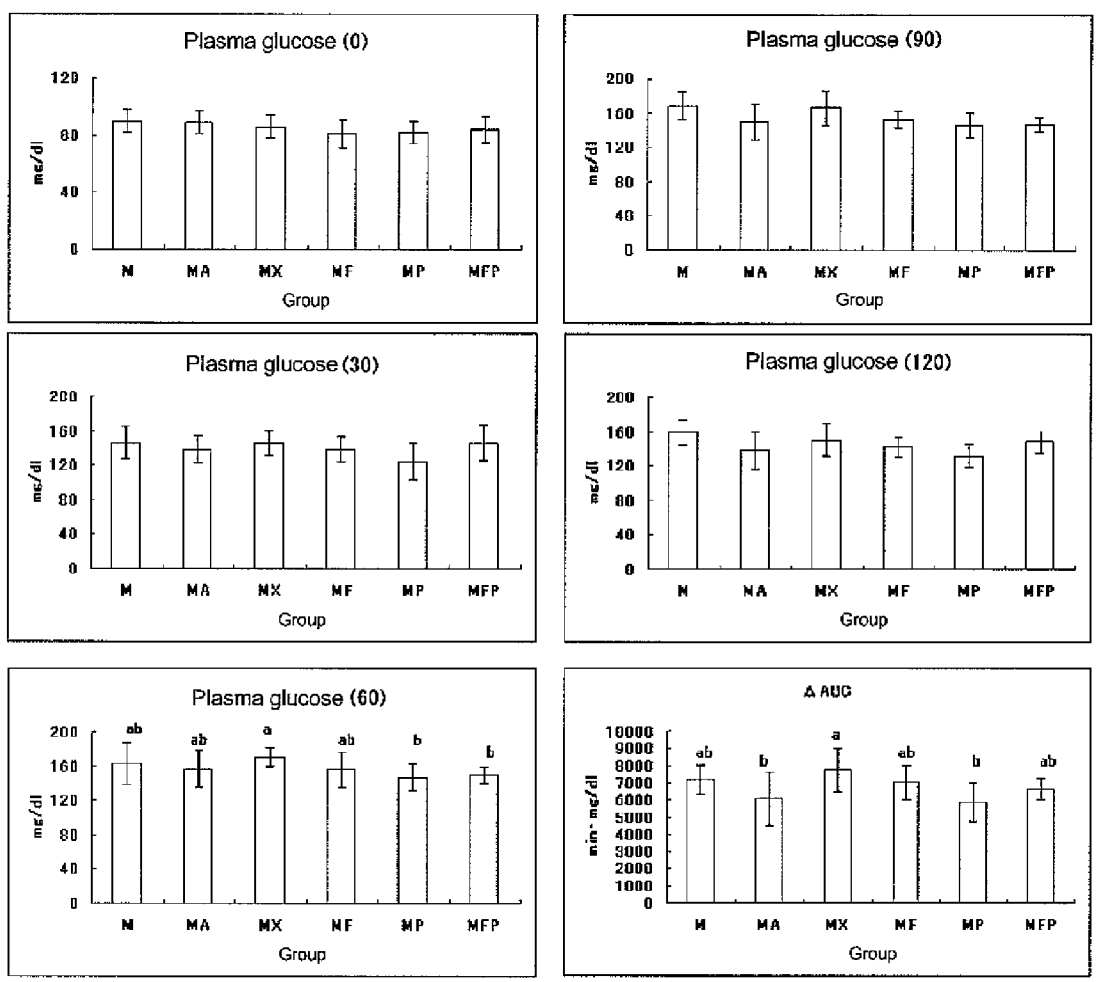
FIG. 5 shows the blood glucose levels 0, 30, 60, 90 and 120 minutes after maltose (2.0 g/kg) (M), and 0.2 g/kg L-arabinose (A), D-xylose (X), D-fructose (F), D-psicose (P) and psico-rare sugar (FP) added to the maltose were given, together with the increment of the area under the curve.
Figure 6:
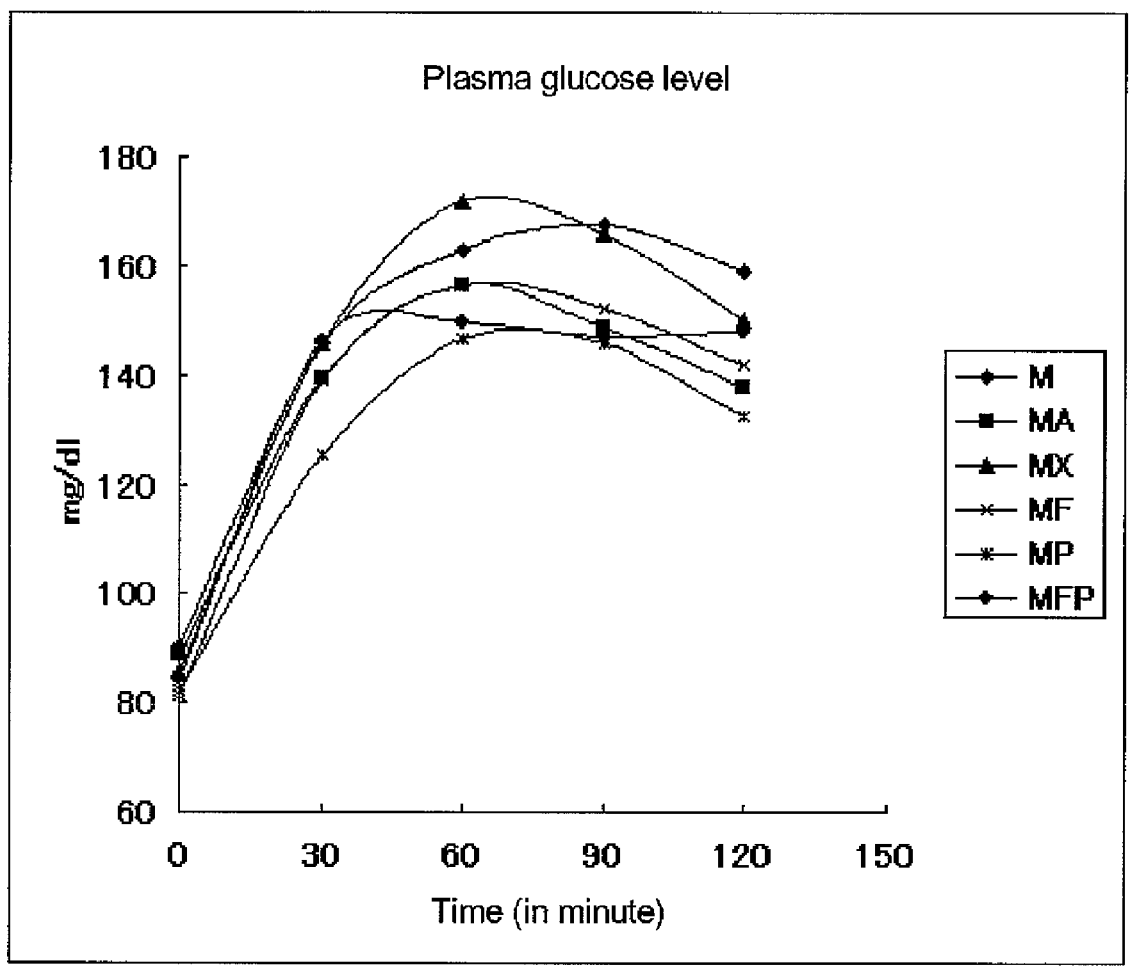
FIG. 6 shows the increase of blood glucose levels after maltose (2.0 g/kg) (M), and 0.2 g/kg L-arabinose (A), D-xylose (X), D-fructose (F), D-psicose (P) and psico-rare sugar (FP) added to the maltose were given.
Figure 7:
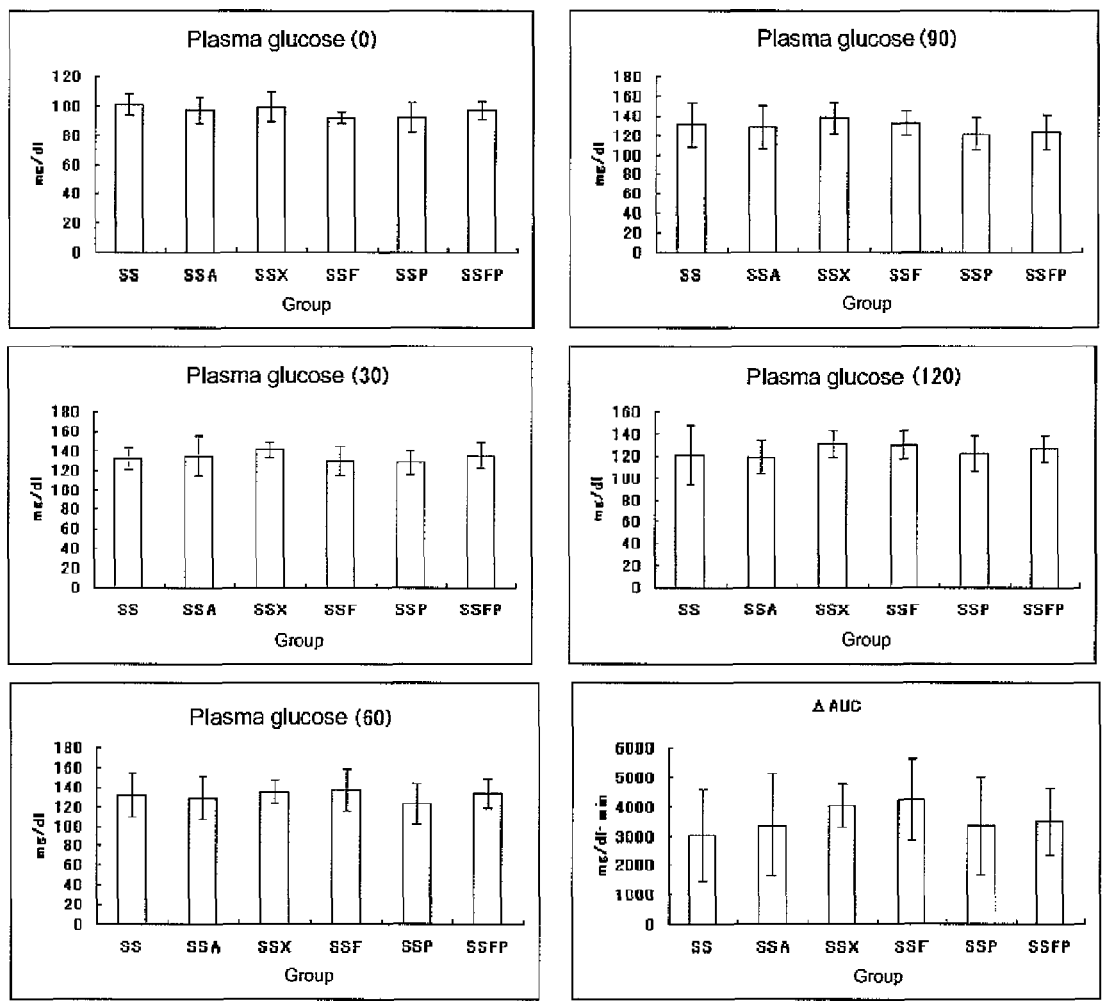
FIG. 7 shows the blood glucose levels 0, 30, 60, 90 and 120 minutes after soluble starch (2.0 g/kg) (SS), and 0.2 g/kg L-arabinose (A), D-xylose (X), D-fructose (F), D-psicose (P) and psico-rare sugar (FP) added to the soluble starch were given, together with the increment of the area under the curve.
Figure 8:
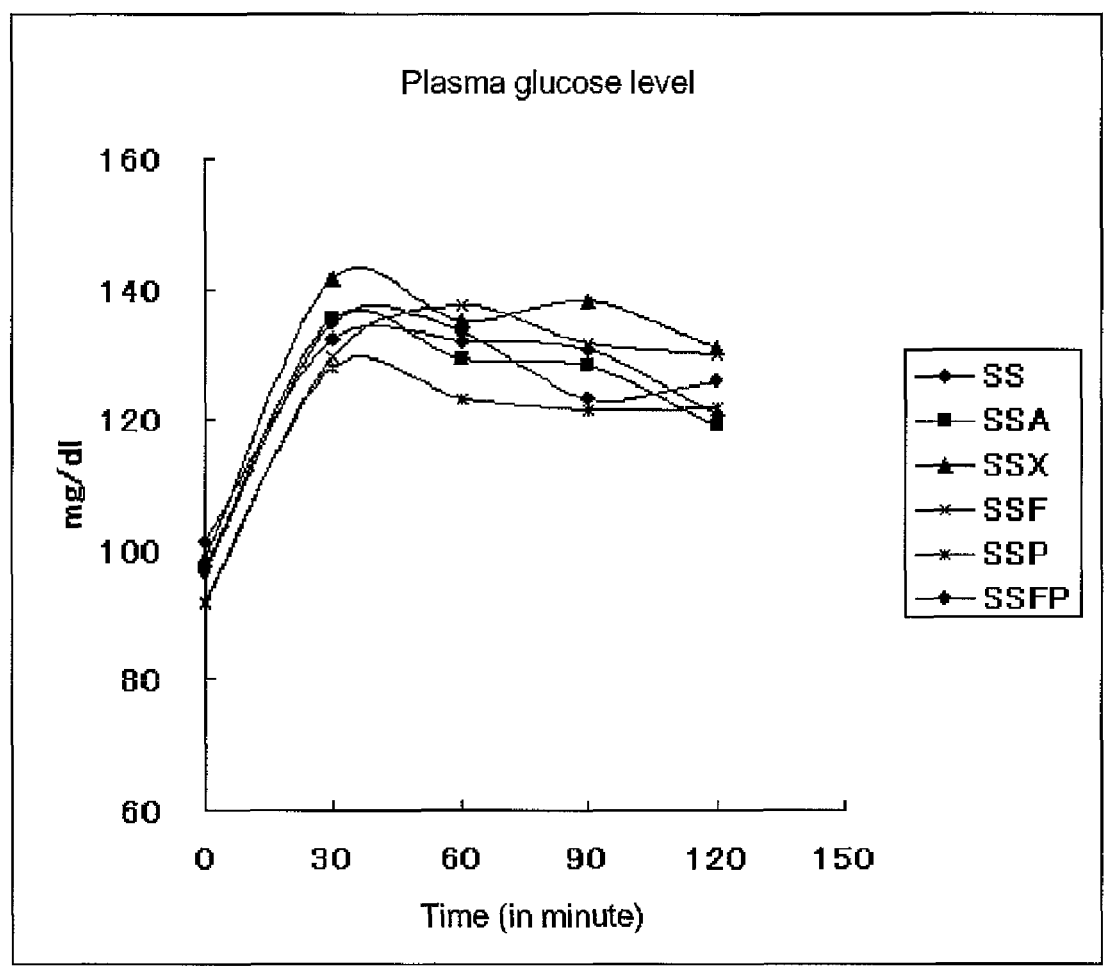
FIG. 8 shows the increase of blood glucose levels after soluble starch (2.0 g/kg) (SS), and 0.2 g/kg L-arabinose (A), D-xylose (X), D-fructose (F), D-psicose (P) and psico-rare sugar (FP) added to the soluble starch were given.

Before the administration and 30, 60, 90, 120 and 180 minutes after the administration, plasma glucose level was assayed. The plasma glucose level 180 minutes later was used to calculate the area under the curve of plasma glucose level (ΔAUC). The results of the experiment 1 are shown in Table 3, and FIGS. 3 and 4. The results of the experiment 2 are shown in Table 4, and FIGS. 5 and 6. The results of the experiment are shown in Table 5, and FIGS. 7 and 8.

TABLE 3

| | Plasma glucose level (mg/dl) | | | | | min$^-$ mg/dl |
|---|---|---|---|---|---|---|
| | 0 | 30 | 60 | 90 | 120 | ΔAUC |
| S | 96 ± 6 ab | 141 ± 16 a | 154 ± 36 a | 148 ± 17 ab | 143 ± 15 | 5579 ± 2003 a |
| SA | 93 ± 7 ab | 139 ± 21 ab | 142 ± 21 ab | 139 ± 14 ab | 142 ± 18 | 4978 ± 1609 a |
| SX | 102 ± 11 a | 123 ± 11 b | 126 ± 12 b | 130 ± 13 b | 137 ± 16 | 2646 ± 685 b |
| SF | 97 ± 10 ab | 134 ± 13 ab | 148 ± 12 ab | 147 ± 9 ab | 141 ± 7 | 4732 ± 886 a |
| SP | 89 ± 9 b | 128 ± 12 ab | 139 ± 13 ab | 150 ± 20 a | 143 ± 28 | 5339 ± 1421 a |
| SFP | 93 ± 7 a | 131 ± 11 ab | 142 ± 16 ab | 141 ± 24 ab | 139 ± 15 | 4696 ± 1393 a |

Mean ± standard deviation

TABLE 4

| | Plasma glucose level (mg/dl) | | | | | min$^-$ mg/dl |
|---|---|---|---|---|---|---|
| | 0 | 30 | 60 | 90 | 120 | ΔAUC |
| M | 90 ± 8 | 146 ± 19 | 163 ± 25 ab | 168 ± 16 | 159 ± 15 | 7202 ± 818 ab |
| MA | 89 ± 7 | 139 ± 16 | 157 ± 22 ab | 149 ± 21 | 138 ± 22 | 6087 ± 1536 b |
| MX | 86 ± 8 | 146 ± 14 | 172 ± 12 a | 166 ± 20 | 150 ± 19 | 7765 ± 1275 a |
| MF | 81 ± 10 | 139 ± 15 | 156 ± 20 ab | 152 ± 10 | 142 ± 12 | 7031 ± 1013 ab |
| MP | 82 ± 8 | 125 ± 21 | 147 ± 16 b | 146 ± 14 | 132 ± 13 | 5887 ± 1121 b |
| MFP | 84 ± 9 | 146 ± 20 | 150 ± 10 b | 147 ± 8 | 148 ± 13 | 6639 ± 631 ab |

Mean ± standard deviation

TABLE 5

| | Plasma glucose level (mg/dl) | | | | | min$^-$ mg/dl |
|---|---|---|---|---|---|---|
| | 0 | 30 | 60 | 90 | 120 | ΔAUC |
| SS | 101 ± 7 | 132 ± 11 | 132 ± 23 | 131 ± 23 | 121 ± 27 | 3011 ± 1501 |
| SSA | 97 ± 9 | 135 ± 20 | 129 ± 22 | 128 ± 22 | 119 ± 15 | 3370 ± 1744 |
| SSX | 99 ± 10 | 141 ± 8 | 135 ± 12 | 138 ± 16 | 131 ± 12 | 4040 ± 729 |
| SSF | 92 ± 4 | 130 ± 15 | 137 ± 21 | 132 ± 13 | 130 ± 13 | 4243 ± 1388 |
| SSP | 91 ± 10 | 128 ± 12 | 123 ± 21 | 121 ± 17 | 122 ± 16 | 3344 ± 1647 |
| SSFP | 97 ± 6 | 135 ± 13 | 133 ± 15 | 123 ± 18 | 126 ± 12 | 3484 ± 1149 |

Mean ± standard deviation

[Discussion]

Figure 4:
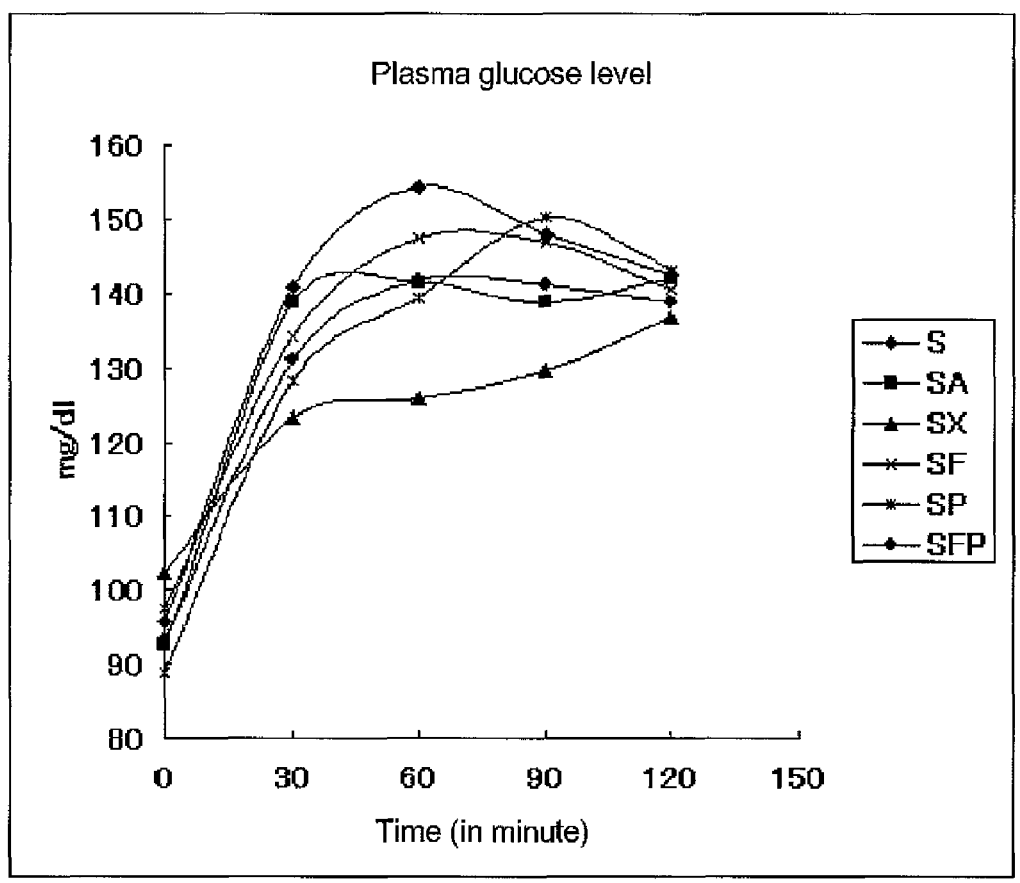
FIG. 4 shows the increase of blood glucose levels after sucrose (2.0 g/kg) (S), and 0.2 g/kg L-arabinose (A), D-xylose (X), D-fructose (F), D-psicose (P) and psico-rare sugar (FP) added to the sucrose were given.

When D-psicose and a mixture of D-fructose and D-psicose (psico-rare sugar) [Discussion] were simultaneously given with sucrose in the experiment 1, the increase of blood glucose level up to 60 minutes after the administration was suppressed, compared with the administration of sucrose alone (Table 3, FIG. 4). Therefore, it is suggested that D-psicose and psico-rare sugar may possibly have an action of inhibiting sucrase. The action was at the same level as that of L-arabinose, of which the action of inhibiting sucrase was verified. Additionally, D-psicose and psico-rare sugar were simultaneously administrated at the maltose administration experiment (experiment 2) and the soluble starch administration experiment (experiment 3), in the same manner as in the experiment 1, to examine the actions of D-psicose and psico-rare sugar to suppress the increase of blood glucose level. Compared with sucrose, it was demonstrated that the effect was low (Tables 4 and 5, and FIGS. 6 and 8). Since D-xylose and L-arabinose scarcely suppressed the increase of blood glucose level, it should be reexamined by raising the doses of D-psicose and psico-rare sugar.

It never occurs that as an application to foods, D-psicose or psico-rare sugar is used instead of starch. On an assumption of using D-psicose and psico-rare sugar in partial replace of sucrose, the experimental results described above should be very significant in view of suppressing the increase of blood glucose level after the intake of saccharide foods.

Example 3

Influence of D-Psicose and Psico-Rare Sugar on the Intra-Day Variation of Plasma Glucose Concentration in Rat It was shown so far that the hepatic glycogen content in rats fed with a 5-% D-psicose diet for a long term was increased. When a sugar solution of sucrose, maltose or soluble starch with addition of 1% D-psicose or psico-rare sugar thereto was given once to rats, the tendency of suppressing the increase of blood glucose level after glucose loading was observed. Further, it was verified at experiments in vitro that D-psicose promoted insulin secretion from pancreatic island cells. Those described above significantly indicate that D-psicose and psico-rare sugar might possibly have a function to suppress the increase of blood glucose level through the following mechanisms: (1) the increase of the uptake of blood glucose into liver and muscle; (2) the inhibition of sugar digestive enzymes in the gastrointestinal tract; (3) the suppression of sugar absorption from the intestinal tract; (4) the stimulation of insulin secretion from pancreas; (5) unknown mechanisms other than (1) through (4). So as to examine the effect of D-psicose and psico-rare sugar on blood glucose level when they were used in daily diets, therefore, feeds with addition of 5% D-psicose and psico-rare sugar were given to rats at given times, to examine the influence on the intra-day variation of plasma glucose concentration in the rats.

[Experimental Conditions]

Forty male Wistar rats of age 3 weeks were preliminarily fed for one week and then divided into 4 groups. Then, a control diet (AIN-76A), and the control diet with addition of 5% D-fructose, the control diet with addition of 5% D-psicose, and the control diet with addition of 5% psico-rare sugar were fed to the rats, twice daily (at 8 to 9 am and at 20 to 21 pm) ad libitum for 8 weeks. At 2 am, 6 am, 10 am, 14 pm, 18 pm and 22 pm on the week 7 or 8 of the feeding, blood was drawn from the tail veins of the rats. Plasma was separated from the blood to assay glucose concentration.

[Results]

Figure 9:
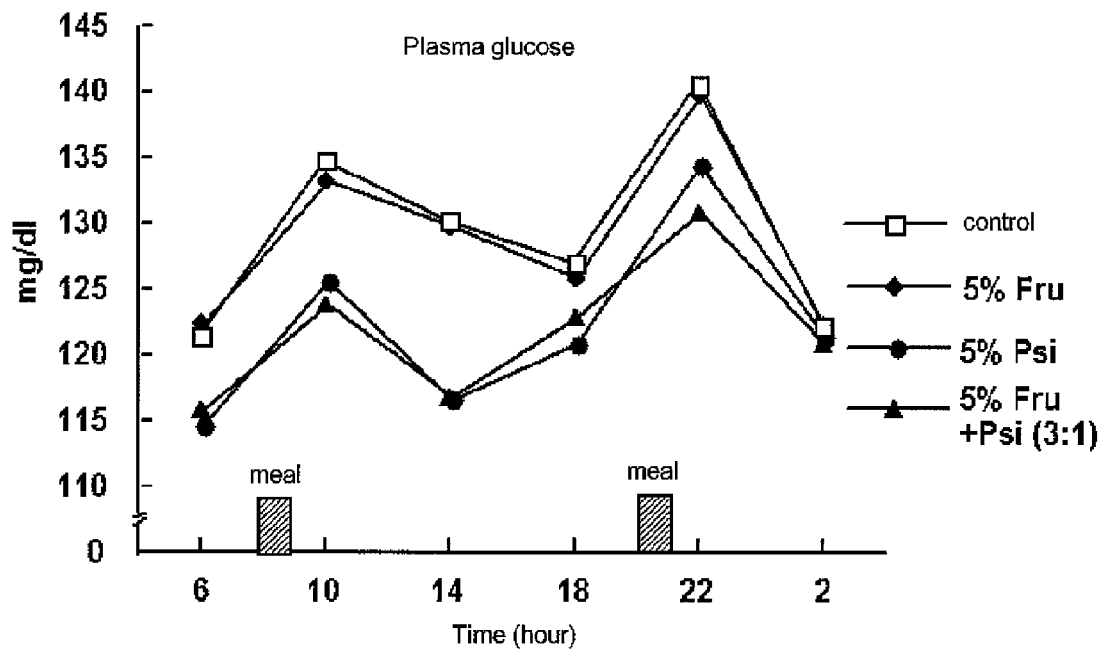
FIG. 9 shows the intra-day variation of plasma glucose concentration in the D-psicose group, the psico-rare sugar group, the control group and the D-fructose group.
Figure 10:
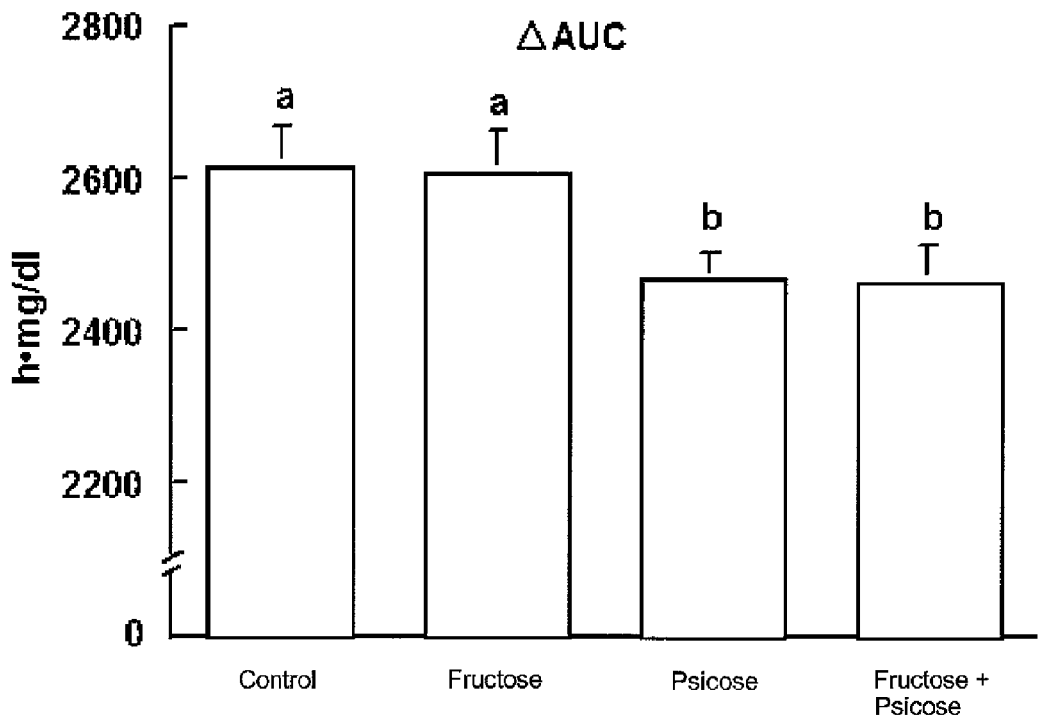
FIG. 10 shows the increment of the area under the curve of plasma glucose concentration in the D-psicose group, the psico-rare sugar group, the control group and the D-fructose group, as based on 8 am.

As shown in FIG. 9, the plasma glucose concentration in the rats of each group was increased after meals. At 10 am and 22 pm, the concentration reached the peak. The plasma glucose concentration was low throughout the day in the D-psicose group and the psico-rare sugar group, compared with the control group and the D-fructose group. Further, the increment of the area under the curve of plasma glucose concentration ($\Delta$AUC) based on 8 am was significantly small in the D-psicose group and the psico-rare sugar group, compared with the control group and the D-fructose group (FIG. 10).

[Discussion]

When the feeds with addition of 5% D-psicose and psico-rare sugar were given to the rats at given times, apparently, the plasma glucose concentration in the rats was low throughout the day. This indicates that the addition of D-psicose and psico-rare sugar to daily diets might possibly suppress the increase of blood glucose level. As clearly shown in the research works so far, D-psicose has the zero energy value. Accordingly, the suppression of plasma glucose concentration in the D-psicose- and psico-rare sugar groups may doubtfully be ascribed to the simple reduction of sugar intake. However, no difference in the intra-day variation of plasma glucose concentration was observed between the D-psicose group and the psico-rare sugar (fructose:psicose=3:1) group where the rats ingested D-psicose at an amount ¼-fold the amount in the rats in the D-psicose group. Therefore, the suppression can never simply be explained on the basis of sugar intake. Alternatively, the mechanism of suppressing the increase of blood glucose level with D-psicose is not yet characterized completely. An unknown function never anticipated may exist. In future, the reproducibility should be verified under the same experimental conditions as to sugar types and energy intake, while the mechanism of suppressing the increase of blood glucose level with D-psicose should necessarily be elucidated in detail at the genetic level and the like.

INDUSTRIAL APPLICABILITY

Simple ingestion of common foods and drinks in mixture with D-psicose enabled the suppression of the intra-day variation of plasma glucose concentration. Using D-psicose alone and a mixture of D-fructose and D-psicose, foods and sweeteners containing common sucrose, starch, and digestive sugars such as oligosaccharides derived from starch could be developed for diabetes mellitus or for diets. Additionally, pharmaceutical products or prophylactic pharmaceutical agents suppressing the abnormal intra-day variation of plasma glucose level could be provided, even when common foods and drinks (under loose diet controls) were incorporated, because the pharmaceutical products or the prophylactic pharmaceutical agents were capable of increasing the uptake of blood glucose into liver and muscle, and/or inhibiting the sugar digestive enzymes in the gastrointestinal tract, and/or stimulating insulin secretion from liver.

Concerning the results of the inhibition of various hydrolases, additionally, the inhibition of various hydrolases with various rare sugar types never examined systematically so far was verified. The inhibitory activity in a considerably wide range may possibly lead to the control of hydrolases with rare sugar and the development of a technique for using such rare sugar. For example, any inhibition of the decomposition of polysaccharides in the natural kingdom may highly possibly enable the storage of polysaccharides.

The invention claimed is:

1. A method for suppressing an abnormal intra-day increase of plasma glucose concentration in a mammal, comprising:
   administering D-psicose at given times to the mammal in need of suppressing a rapid increase of blood glucose level associated an intake of D-glucose from foods and drinks and suppressing the abnormal increase of plasma glucose concentration throughout the day,
   wherein D-psicose is administered for 7 weeks.

2. The method according to claim 1, wherein said suppressing the abnormal intra-day increase of plasma glucose concentration is based on at least one of:
   (i) enhancing the uptake of blood glucose into the liver and muscle of the mammal,
   (ii) inhibiting sugar digestive enzymes in the gastrointestinal tract of the mammal,
   (iii) inhibiting sugar absorption from the gastrointestinal tract of the mammal, and
   (iv) stimulating insulin secretion from the pancreas of the mammal.

3. The method according to claim 2, wherein D-psicose is blended in a composition to a content of 0.1 to 50% by weight of the total carbohydrate amount in the composition.

4. The method according to claim 3, wherein the composition is a food containing carbohydrates and D-psicose, and wherein D-psicose is 0.1 to 50% by weight of the total carbohydrate amount in the food.

5. The method according to claim 3, wherein the composition is a drinkable liquid containing D-psicose, and wherein D-psicose is 0.1 to 50% by weight of the total carbohydrate amount in the composition.

6. The method according to claim 3, wherein the composition is a feed containing carbohydrates and D-psicose, and wherein D-psicose is 0.1 to 50% by weight of the total carbohydrate amount in the feed.

7. The method according to claim 1, wherein said administrating maintains the suppressed plasma glucose concentration throughout the day.

8. The method according to claim 1, wherein D-psicose is administered at least twice a day and on consecutive days.

* * * * *